United States Patent
Barrows

(10) Patent No.: US 6,884,427 B1
(45) Date of Patent: Apr. 26, 2005

(54) FILAMENTARY MEANS FOR INTRODUCING AGENTS INTO TISSUE OF A LIVING HOST

(75) Inventor: Thomas H. Barrows, Austell, GA (US)

(73) Assignee: Aderans Research Institute, Inc., Beverly Hills, CA (US)

(*) Notice: Subject to any disclaimer, the term of this patent is extended or adjusted under 35 U.S.C. 154(b) by 0 days.

(21) Appl. No.: 09/890,888

(22) PCT Filed: Feb. 8, 2000

(86) PCT No.: PCT/US00/03488

§ 371 (c)(1),
(2), (4) Date: Aug. 7, 2001

(87) PCT Pub. No.: WO00/45736

PCT Pub. Date: Aug. 10, 2000

Related U.S. Application Data

(60) Provisional application No. 60/119,082, filed on Feb. 8, 1999.

(51) Int. Cl.⁷ ............................ A61F 13/00; A61F 2/00; A61K 9/14
(52) U.S. Cl. .................. 424/422; 424/423; 424/449; 424/486
(58) Field of Search ................ 424/422, 423, 424/449, 486, 426, 443

(56) References Cited

U.S. PATENT DOCUMENTS

| | | | |
|---|---|---|---|
| 4,104,195 A | * | 8/1978 | Ley et al. ............... 516/15 |
| 5,486,593 A | * | 1/1996 | Tang et al. ............. 528/370 |
| 5,545,208 A | * | 8/1996 | Wolff et al. ........... 623/1.22 |
| 5,599,552 A | * | 2/1997 | Dunn et al. ............. 424/423 |
| 5,847,012 A | * | 12/1998 | Shalaby et al. ........... 521/61 |
| 5,898,040 A | | 4/1999 | Shalaby et al. |
| 5,993,374 A | | 11/1999 | Kick |
| 5,997,468 A | | 12/1999 | Wolff et al. |
| 6,027,744 A | * | 2/2000 | Vacanti et al. .......... 424/426 |
| 2002/0049426 A1 | * | 4/2002 | Butler et al. .......... 604/892.1 |
| 2004/0039438 A1 | * | 2/2004 | Alt ....................... 623/1.15 |

OTHER PUBLICATIONS

Peter X. Ma and Ruiyun Zhang, Synthetic nano–scale fibrous extracellular matrix, J. Biomed. Materials Res. 46(1):60–72 (Jul. 1999).
Seigi Arase, et al., Tokushima J. exp. Med 36: 87–95 (1989).
Edoardo Raposio, et al., Follicular Bisection in Hair Transplantation Surgery: An in Vitro Model, Plastic and Reconstructive Surgery, pp. 221–226 (Jul. 1998).
C.W. Patrick Jr., A. G. Mikos and LV. McIntire, eds., Prospects of Tissue Engineering, Frontiers in Tissue Engineering, Elsevier Science, Inc., New York, 1998.
A.J. Reynolds, C. Lawrence, P.R. Caerhalmi–Friedman, A.M. Christiano, and C.A.B. Jahoda, Nature 402: 33–34, Nov. 4, 1999.

* cited by examiner

Primary Examiner—James M. Spear
Assistant Examiner—Isis Ghali
(74) Attorney, Agent, or Firm—Michael Best & Friedrich, LLP

(57) ABSTRACT

The present invention provides a filamentary structure for the introduction of agents into a living host, comprising a filament comprising a solid core and a porous sheath which coats at least a portion of the solid core. When the filamentary structure is to be permanently implanted into a living host, both the solid core and the porous sheath are bioabsorbable. When the filamentary structure is to be temporarily implanted into the skin of a living host to deliver agents, such as cells, therein, the porous sheath is preferably bioabsorbable but the core need only be biocompatible, not bioabsorabable. The devices and methods of the present invention enable one to regenerate hair follicles, to introduce genetically altered cells or encapsulated cells to a living host transdermally, to regenerate bones, and to deliver drugs transdermally.

22 Claims, 9 Drawing Sheets

FILAMENTARY MEANS FOR INTRODUCING AGENTS INTO TISSUE OF A LIVING HOST

CROSS-REFERENCE TO RELATED APPLICATIONS

This application claims the benefit of U.S. Provisional Application No. 60/119,082, filed Feb. 8, 1999.

STATEMENT REGARDING FEDERALLY SPONSORED RESEARCH OR DEVELOPMENT

Not Applicable.

BACKGROUND OF THE INVENTION

This invention relates to means for the delivery of agents into a living body. More specifically it relates to filaments comprising porous bioabsorbable polymers, which facilitate the implantation of living cells and other agents, such as drugs, into specific tissues, including skin and bone, for the purposes of site-specific drug or cell release, gene therapy, and the facilitation of the regeneration of tissue, including the regeneration of bone and hair tissue.

Current means for the delivery of agents such as drugs, growth factors, genetically modified cells, and the like into a living body include various pharmaceutical dosage forms, such as ingestable tablets, patches designed to deliver agents transdermally, and surgically implantable devices designed to deliver agents to an implant site. Early implantable devices were not bioabsorbable, and had to be surgically removed after they had been used for their intended purpose. More recently, implants of bioabsorbable polymers have been developed. Such implants are absorbed by the host in which they are implanted after, or in the course of serving their intended purpose. One such device, disclosed by Dunn et al. in U.S. Pat. No. 5,599,552 ("Dunn et al. '552"), is an implant of a porous core of a bioabsorbable polymer, surrounded by a non-porous surface skin of the bioabsorbable polymer. That particular device is designed for use in delivering a biologically active agent to a living host when implanted therein. The device disclosed by Dunn et al. '552 is also designed so that it can act as a matrix to promote tissue regeneration at an implant site. (Id.)

Two other types of implantable devices of bioabsorbable polymers are disclosed in U.S. Pat. No. 5,847,012 ("Shalaby et al. '012"). One such device consists of a bioabsorbable microporous polymeric foam with open-cell pores. The other such device consist of an implant with a modified surface, consisting of a surface layer of bioabsorbable microporous polymeric foam with open-cell pores. (Id.) The implants of Shalaby et al., '012 are designed to accept the agent to be delivered, such as a medicament or growth factor, and to deliver the agent to a living patient after implantation therein.

Textile technologies have also been adapted for use in making biodegradable woven fabrics as tissue engineering scaffolds. See Introduction of Peter X. Ma and Ruiyun Zhang in *J. Biomed. Materials Res.* 46(1):60–72 (July 1999). The diameter of the biodegradable fibers used to produce such woven scaffolds is about 15 $\mu$m. Ma and Zhang demonstrated that fibers with a considerably smaller diameter, ranging from 50 to 500 nm could be created from biodegradable aliphatic polyesters. The woven scaffolds of Ma and Zhang, and those described therein were designed for use as scaffolds, and not as means for delivery of agents to tissue.

The advantage of all the bioabsorbable devices described above was that they could be implanted into a living host and left in place to do what they were designed to do, without the necessity of removal therefrom. The devices would be absorbed by the host over time. Of the bioabsorbable devices disclosed in the references described above, only the device of Dunn et al. '552 is designed to act as both scaffolding and delivery agent. That device has limited flexibility, because of the way it is designed. What is needed is a bioabsorbable fiber or composite thereof, which is capable of being processed into a scaffolding for tissue formation, and which is capable of delivering agents to a living host when implanted therein. The present invention meets that need.

The present invention also meets a need for an inexpensive and relatively painless means for regenerating hair. Plastic surgery is one of the few means available to correct male pattern baldness, today. In that particular surgical procedure, the amount of permanently hair-bearing donor tissue available can significantly affect the feasibility and outcome of the procedure. In vitro growth techniques have been developed to increase the amount of hair follicle cells available for use in such procedures. See, e.g., Seigi Arase, et al. Tokushima *J. exp. Med* 36: 87–95 (1989); and Edoardo Raposio, et al. *Plastic and Reconstructive Surgery* pp. 221–226 (July 1998). What is needed is a relatively painless and inexpensive means for the regeneration of hair, one which does not involve plastic surgery or other painful and expensive implantation techniques, preferably, a technique which produces hair which looks realistic and similar to other hair on the same host. The present invention utilizes a modified form of the bioabsorbable polymeric means developed for use in implantable devices, as described above, to deliver hair follicle cells transdermally and to promote the regeneration of hair therein.

As is shown in the next section, below, the present invention provides a new means for the introduction of agents into a living host, a means which offers several advantages over known means in use today, such as those described briefly above.

BRIEF SUMMARY OF THE INVENTION

The present invention provides a filamentary means for the introduction of agents into a living host, comprising a filament comprising a solid core and a porous sheath which coats at least a portion of the solid core. When the filamentary means is to be permanently implanted into a living host, both the solid core and the porous sheath are bioabsorbable. When the filamentary means is to be temporarily implanted into the skin of a living host to deliver agents, such as cells, therein, the porous sheath is preferably bioabsorbable but the core need only be biocompatable, not bioabsorabable.

The solid core is preferably wire when the filamentary means is designed to be used to deliver an agent, such as hair follicle cells, into the skin of a living host. The solid core is preferably glass or ceramic when the filamentary means is to be used to deliver an agent, such as cells or pharmaceutical agents, into bone through implantation of the filamentary means into the body of the host.

The porous sheath is preferably in the form of reticulated foam that is well adhered to the core but is capable of separating from the core after a period of several days in vivo. When the agent to be delivered with the filamentary means is a drug, the porous sheath is preferably in the form of a hydrogel and the porosity is on a molecular size scale.

The filamentary means of the present invention provides means for delivery of cells or other agents from outside the body of a living host into the skin of the host, such as a mammal, with minimal trauma to the host. When the filamentary means is comprised of a bioabsorbable core with a bioabsorbable porous sheath which coats at least a portion of the core, the filamentary means can be implanted into specific tissue within a living host and used to deliver agents to the specific tissue when implanted therein. The implantable embodiment of the filamentary means can serve as a surface for osteoblast attachment and as a scaffold for bone regeneration upon implantation into the bone tissue of a living host. The above-cited features of the filamentary means of the present invention enable it to be used for a variety of purposes including, but not limited to, hair follicle regeneration, gene therapy and encapsulated cell delivery, bone regeneration, and trans-dermal drug delivery.

Another embodiment of the present invention is a method of making a filamentary means for introducing an agent into a living host, comprising providing a solid filament, a bioabsorbable polymer, and a pore-forming agent, mixing the bioabsorbable polymer with the pore-forming agent, coating the resulting mixture onto at least a portion of the filament, and substantially removing or decomposing the pore-forming agent.

Other embodiments of the present invention include devices designed to enable one to use the filamentary means of the invention to deliver various agents into a living host, methods for making such devices, and methods for using the devices of the present invention to deliver agents into a living host. The devices and methods of the present invention enable one to regenerate hair follicles, to introduce genetically altered cells or encapsulated cells to a living host transdermally, to regenerate bones, and to deliver drugs transdermally. The devices and methods of the present invention are described briefly below.

One embodiment of the present invention is a hair follicle cell implant device designed to implant hair follicle cells into the skin of a living host. Another embodiment of the hair follicle cell implant device of the present invention is a method of making the implant device. Yet another embodiment is a method of using the implant device to deliver hair follicle cells to implant such cells into the skin of a living host, preferably into the scalp of a human being suffering from male pattern baldness. The hair follicle cell implant device of the present invention comprises a plurality of filaments, each of which has a first end and a second end and comprises a solid core and a bioabsorbable porous sheath which coats the solid core, and a semi-rigid backing with the second end of each filament embedded therein such that the first end of each filament protrudes therefrom. The first end of each filament protrudes from the semi-rigid backing a sufficient length to penetrate the skin of a living host when the device is in contact therewith. The filaments are preferably spaced the same distance apart as hairs on the normal surface of skin of the living host.

The hair follicle cell implant device of the present invention is preferably made by the steps comprising: providing a plurality of filaments, each of which has a first end and a second end and comprises a solid core and a bioabsorbable porous sheath which coats the solid core; and fixing the second end of each of the plurality of filaments in a semi-rigid backing such that the filaments are spaced the same distance apart as hairs on the skin of a normal living host, and such that the second end of each of the plurality of filaments protrudes from the semi-rigid backing at a depth sufficient to penetrate the skin of the living host when placed into contact therewith.

The hair follicle cell implant device is used to stimulate hair growth according to a method comprising: seeding the boabsorbable porous sheath at the first end of each filament with hair follicle cells, introducing the cells into the skin of a living host by puncturing the skin with the first end of each filament, and removing the device from the skin after sufficient time has passed to allow the porous coating within the skin to separate from the solid core of each filament, leaving the porous coating and hair follicle cells in the skin.

One advantage of the hair follicle cell implant device and methods of making and using the same is that they provide means for delivering cultured cells harvested from hair follicles into the skin of a host, such as the bald scalp of a human male, such that said cells are able to generate new hair follicles. The new hair follicles, once generated, will continue to grow and be maintained in the dermis of the host. Another advantage of these embodiments of the present invention is that they provide a means for the simultaneous implantation of hair follicle cells into multiple sites in the skin such that the spacing between each individual implant is approximately the same as the spacing between the hair follicles in the normal scalp. Regenerated hair grown from follicle cells implanted in such a pattern have a natural, cosmetically appealing look. Thus, the present invention provides an efficient device and method of restoring a normal density of normally functioning hair follicles in the hairless scalp as an effective, natural, and permanent remedy for baldness.

In another aspect, the present invention is a method of using the filamentary means of the present invention to deliver genetically modified cells into normal healthy skin, such that the cells deliver a therapeutically efficacious systemic level of the desired gene product. In this embodiment, a filamentary means comprising a filament comprising a solid core having a first end and a second end and a porous sheath which coats at least the first end of the solid core, wherein the porous sheath is bioabsorbable, is used to deliver genetically modified cells into the skin of a living host, according to the steps comprising: providing the filament, seeding the porous sheath at the first end of the filament with the genetically transformed cells, introducing the cells into the skin of the living host by puncturing the skin with the first end of the filament, and removing the filament from the skin after sufficient time has passed to allow the porous coating to separate from the filament at the first end of the solid core of the filament, leaving the porous coating and genetically transformed cells in the skin.

An advantage of this embodiment of the present invention is that it provides a means for the delivery of encapsulated or otherwise immunoprotected cells into normal healthy skin such that the cells delivered therewith take over the function of cells in other organs that have lost their required function due to disease such as diabetes. Another advantage of this embodiment of the invention is that it also provides a means for the delivery of genetically modified cells into diseased or ulcerated skin to treat the disease or provide growth factors to heal the ulcers.

An advantage of another embodiment of the present invention is that it provides that a rigid scaffold with a highly porous surface, which can be implanted into a living host, and maintained for a long enough period of time to facilitate new bone formation. The porous surface enables this embodiment of the invention to be used as a means for the delivery of osteoblasts and/or other osteoinductive substances into bone defects, gaps, or fusion devices.

Another embodiment of the present invention is a device for delivery of a drug through the skin, comprising: a plurality of filaments each of which has a fist end and a second end and comprises a solid core and a bioabsorbable polymer sheath in which the drug is soluble and permeable; a semi-rigid backing having a first side and a second side, wherein the second side of the semi-rigid backing defines a reservoir, wherein each of the plurality of filaments is fixed in the semi-rigid backing such that the first end of each filament protrudes from the first side of the semi-rigid backing and the second end of each filament extends to the second side of the semi-rigid backing such that it is in contact with the reservoir. An advantage to the device of delivery of a drug through the skin of the present invention is that it provides a means for the continuous delivery of drugs through the skin that normally do not penetrate skin from a reservoir placed on the surface of the skin.

Other advantages of the filamentary means for the delivery of agents into a living body of the present invention will become apparent upon disclosure of the invention as described below.

DETAILED DESCRIPTION OF THE INVENTION

Figures 1A, 1B:
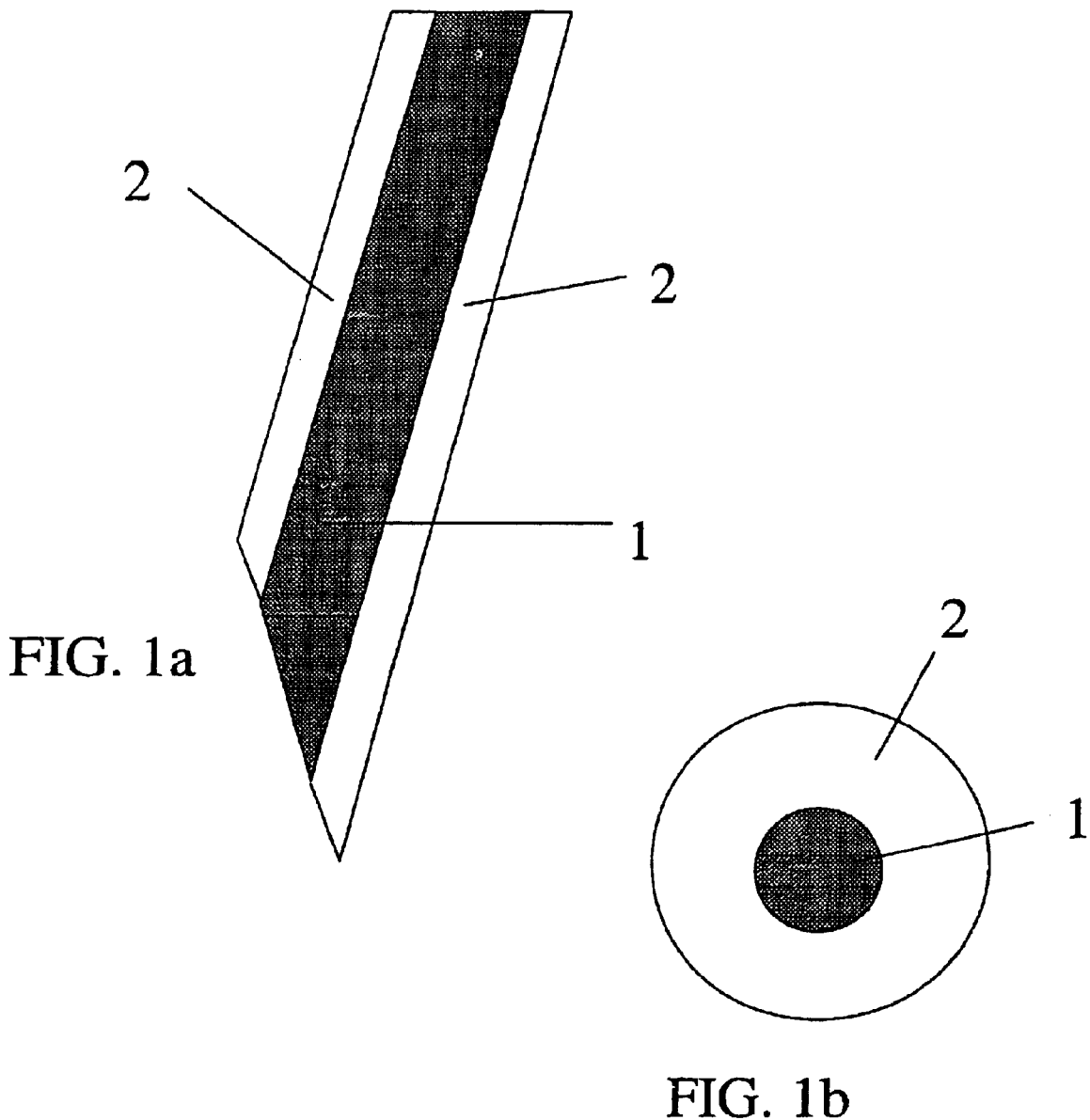
FIG. 1a is a schematic view of the filament in longitudinal section, showing the solid core (1) and the porous sheath (2), without details of the porous structure.
FIG. 1b is a schematic view of the filament in transverse section, showing the solid core (1) and porous sheath (2).

The present invention provides filamentary means for delivery of various agents into a living host, a means comprising a filament comprising a solid core and a bioabsorbable porous sheath. When the solid core is made of bioabsorbable material, it is preferably material selected from the group consisting of glass, ceramic, and polymeric material. When the solid core is made of a biocompatible material, it is preferably material selected from the group consisting of metals or alloys containing the elements of iron, nickel, aluminum, chromium, cobalt, titanium, vanadium, molybdenum, gold, and platinum. The core of the filamentary means is preferably made of bioabsorbable material when the filamentary means is to be used as or as part of an implant to be permanently implanted into the body of a living host. The core of the filamentary means is preferably made of biocompatable material when the filamentary means is to be used in the transdermal delivery of an agent. The bioabsorbable nature of the material of the core and sheath of the preferred permanent implant devices of the present invention enable the living host into which they are implanted to absorb the implant over time.

The bioabsorbable porous sheath is preferably comprised of a bioabsorbable polymer, more preferably a bioabsorbable polymer selected from the group consisting of poly (lactic acid), poly(glycolic acid), poly(trimethylene carbonate), poly(amino acid)s, tyrosine-derived poly (carbonate)s, poly(carbonate)s, poly(caprolactone), poly (para-dioxanone), poly(ester)s, poly(ester-amide)s, poly (anhydride)s, poly(ortho ester)s, collagen, gelatin, serum albumin, proteins, carbohydrates, poly(ethylene glycol)s, poly(propylene glycol)s, poly(acrylate ester)s, poly (methacrylate ester)s, poly(vinyl alcohol), and copolymers, blends and mixtures of said polymers.

A particularly preferred bioabsorbable polymer for use as a bioabsorbable porous sheath coating on the solid core is poly(lactic acid) or any of the various known copolymers of lactic and glycolic acids such as a copolymer of L-lactide with dl-lactide known as poly(L/DL-lactide). Such bioabsorbable polymers have a long history of safe clinical use in the form of synthetic absorbable suture materials and have been utilized successfully in a number tissue engineering research experiments. Moreover, these polymers are thermoplastic and soluble in a variety of organic solvents enabling their use in coating wires by known extrusion and solution based processes.

An advantageous feature of the filamentary means of the present invention is the porosity of the bioabsorbable porous sheath. Here again the application of proven technology can be beneficial in achieving the desired pore size and void volume of the porous sheath. A preferred method for creating porosity in the bioabsorbable polymer coating involves the use of "blowing agents". These are chemical additives that decompose at known temperatures with the liberation of gases that cause foaming in the molten polymer and porosity in the resultant cooled material. A number of useful blowing agents are commercially available under the trade name of Celogen™ (Uniroyal Chemical Co.). One example of a traditional blowing agent is azodicarbonamide. Another blowing agent that may be especially useful in the present invention due to its compatibility with bioabsorbable polymers is urea dicarboxylic acid anhydride, described in U.S. Pat. No. 4,104,195, the teachings of which are incorporated herein. The use of blowing agents can produce both open cell and closed cell foams. In the present invention open cells are desired and closed cells are to be avoided. Thus the conditions used in the manufacture of the porous coating are preferably optimized to achieve an open cell structure known as "reticulated" foam.

The filamentary means of the present invention can be designed to deliver a variety of different agents, depending on the porosity and composition of the porous sheath. The agent delivered with the filamentary means of the present invention is preferably selected from the group consisting of: cells, growth factors, drugs, recombinant molecules, cell signaling molecules, cell recognition factors, cell binding site molecules, cell attachment molecules, cell adhesion molecules, proteins, glycoproteins, carbohydrates, naturally occurring polymers, synthetic polymers, semi-synthetic polymers, and recombinant polymers.

The porous sheath of the filamentary means is designed to deliver the agent into a living host when the agent is coated on the outer surface of the sheath, or mixed, dissolved, or imbedded within the porous sheath. The porous sheath preferably defines pores which are substantially interconnected and large enough to admit the agent. The pores of the porous sheath are preferably open pores produced using blowing agents, as described below. The pores are preferably large enough to admit molecules ranging in molecular weight from about 100 to about 3,000,000 Daltons, more preferably ranging from about 500 to about 100,000 Daltons. Alternatively, the porous sheath preferably defines pores which range in size from about 0.1 micrometers to about 500 micrometers, more preferably which range in size from about 10 to 200 micrometers.

The extent to which the porous sheath coats the core of the filamentary means varies according to the application in which the filamentary means is to be used. For example, when only one end of a filament is to be combined with an agent before being used to implant the agent into a living host by puncture the skin of the host, only that end of the filament need include the porous sheath. In contrast, when an entire filament is to be used to deliver an agent to a host, such as happens when the entire filament is implanted into the host, the entire length of the core of the filament is preferably coated with the porous sheath.

A discussion of more specific preferred features of the filamentary means of the present invention, as used in additional embodiments of the present invention follows. It is contemplated that additional advantages and features of the present invention will become evident to one of ordinary skill in the art of the present invention upon review of the present disclosure.

Hair Follicle Regeneration.

One of the embodiments of the present invention provides materials and methods for a tissue engineering approach to hair follicle regeneration. Tissue engineering is generally defined as the technology of restoring defective or missing tissues or organs by the implantation of living cells that have been cultured and multiplied outside the body. A more detailed description of the philosophy and techniques of tissue engineering has been published by C. W. Patrick Jr., A. G. Mikos and L V. McIntire, eds., *Frontiers in Tissue Engineering*, Elsevier Science, Inc., New York, 1998, the teachings of which are incorporated herein.

In a preferred embodiment of the present invention, cells harvested from a few hair follicles are multiplied in vitro by tissue culture techniques and re-implanted into bald skin, thereby generating hundreds of hairs from each hair that is harvested to seed the tissue cultures. A remarkable feature of the present invention is the means by which the appropriate cells are introduced into the skin and the unique ability of the implants to facilitate regeneration of the cellular architecture of normal hair follicles.

The hair follicle cell implant device of the present invention is comprised of three preferred parts: (1) a fine stainless steel or other suitably biocompatible wire or stiff fiber that is capable of easily penetrating the skin; (2) a porous coating on said wire comprised of a bioabsorbable polymer that is suitable as a support for cell attachment and growth; and (3) a means for the semi-rigid backing of multiple coated wires in an array to facilitate the implantation of said multitude of wires into the skin and their subsequent removal at an appropriate time post-implantation. The stainless steel wire is the core, and the porous coating the porous sheath of this particular embodiment of a filament of the present invention. The wire and filament produced therefrom have a first end and a second end.

The porous bioabsorbable coating on the wire can be selected from a variety of known polymers and the process of applying the coating and forming the porous structure can be selected from a variety of known processes. Similarly, the degree of porosity, the thickness of the coating, and the diameter of the wire can be varied as desired to obtain the optimum performance of the implant and the most efficient neogenesis of hair follicles. In general, the wire diameter will be similar to the diameter of the hair that is to be regenerated for each individual patient. The thickness of the coating will be equivalent to the sum of the various cellular layers comprising the hair follicle that surround a normal hair shaft. The preferred coating will not cover the entire length of the wire. Instead, the coating will begin at a position distal to the first end of the wire, depending on the desired depth at which the cells are to be delivered from that end of the wire.

The first end of the filament is preferably sharp to facilitate entry into the skin of the living host. The sharp shape of the first end can be produced by cutting the first end of the wire off at an angle after the wire is coated with the porous bioabsorbable polymer. However, it is more preferably produced by cutting the first end of the wire at an angle prior to coating the first end with the porous bioabsorbable polymer. The coating preferably does not cover the most distal end of the first end of the wire, in order to allow first end of the wire to enter the skin of a living host using the lowest possible injection force.

A preferred wire for use as the core of the filamentary means of hair follicle cell implant device of the present invention is 316L stainless steel. This particular metal alloy has been widely used clinically in the form of surgical skin staples. A typical diameter of wire for use in this invention that is similar to the diameter of human hair is about 3 to 5 thousandths of an inch. Although such a fine wire might seem too flexible for use in penetration of the skin, the depth of penetration needed is shallow enough to permit the implant to have a relatively low aspect ratio (length divided by diameter) such that bending of the wire is unlikely to occur. In addition, penetration of the skin by such a fine wire sharpened by cutting the end off at an angle will be relatively atraumatic. As an aid to penetration and patient comfort, the skin can first be anesthetized and softened by the application of an analgesic lotion and covered with an occlusive dressing for about an hour prior to implantation of the wires.

A novel method of creating the porous sheath on the wire core to create the filaments used to make the device of the present invention is to select a wire core that can be heated electrically, such as nickel-chromium alloy wire. The wire core is then coated with a mixture of polymer and blowing agent below the decomposition temperature of the blowing agent. The porous coating is then formed by connecting the wire to an electrical current to obtain the precise rate of heating, duration of heating time, and ultimate temperature to produce the desired effect. Conducting this operation under the flow of an inert atmosphere of nitrogen or argon, or submerged in oil, is beneficial in protecting the polymer from oxidation and providing rapid cooling and solidification of the highly porous structure created at the instant of blowing agent decomposition.

Figure 2:
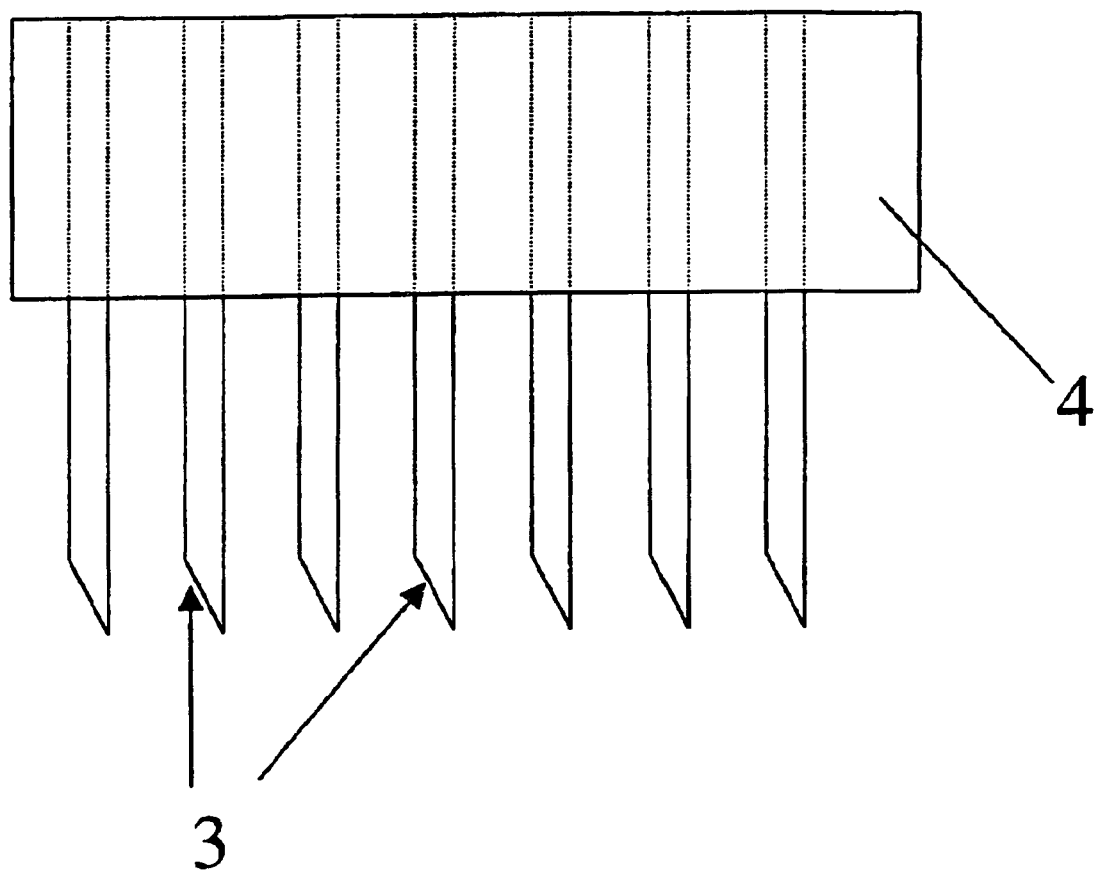
FIG. 2 is a schematic sectional view of a hair implant device with an array of the core-sheath filaments (3) shown imbedded in a semi-rigid backing (4) which maintains the filaments in a stable, rigid parallel configuration.
Figure 3:
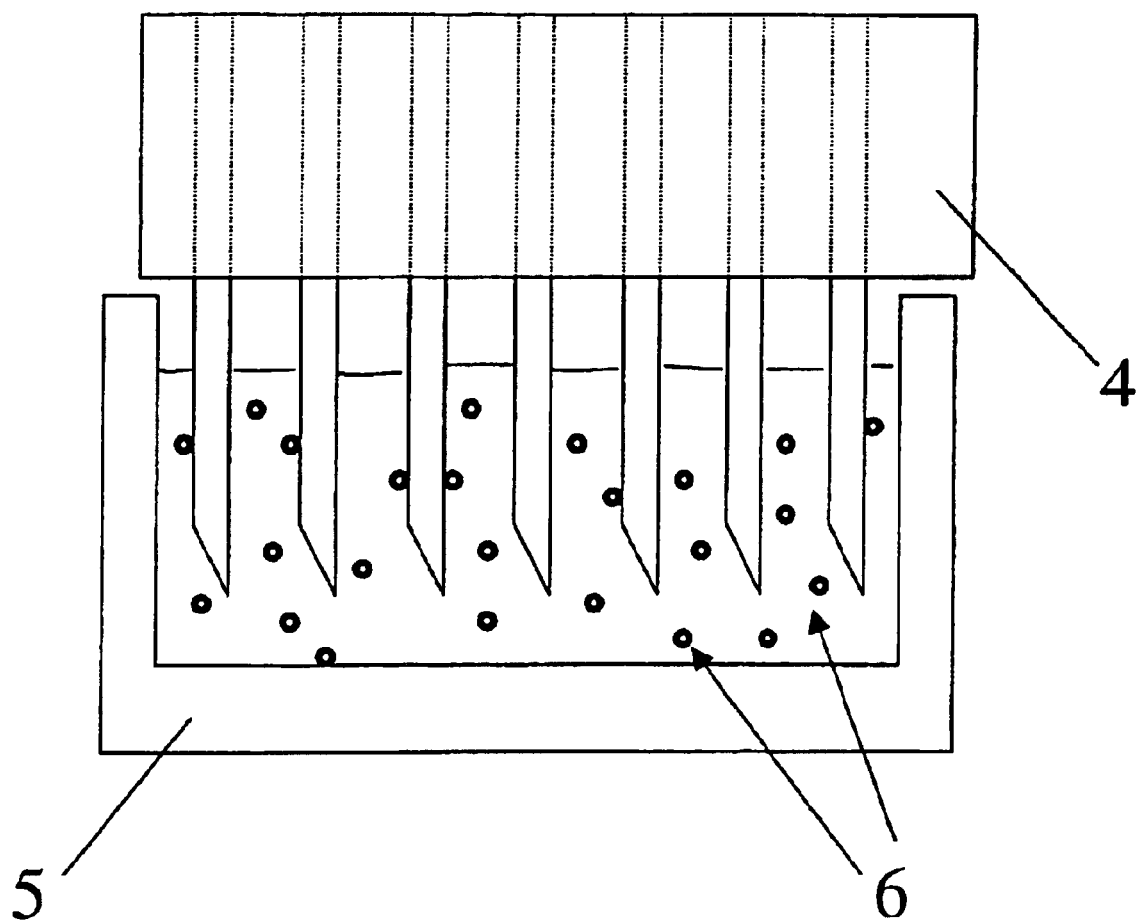
FIG. 3 is a schematic sectional view of the hair implant device with the array of filaments (3) imbedded in the semi-rigid backing (4), immersed in a vessel (5) containing a tissue culture broth of free floating cells (6) derived from the hair follicles of a living host.
Figure 4A:
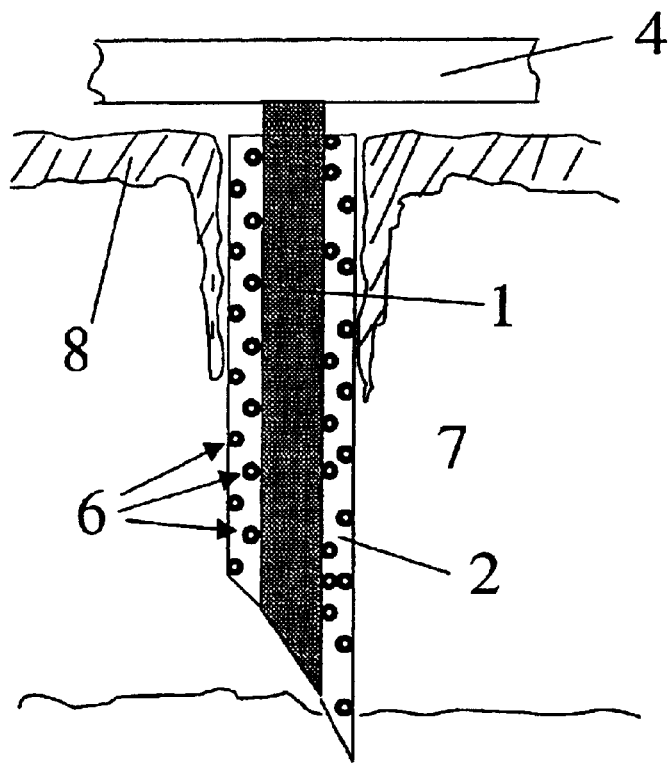
FIG. 4a depicts a sectional view of a single-filament with cultured cells (6) contained within the porous sheath (2) surrounding the solid core (1) of a filament, which has been implanted in the skin through the full thickness of the dermis (7). The filament has been present in the skin for several days during which time the epidermis (8) has begun to grow down the outside of the filament.
Figure 4B:
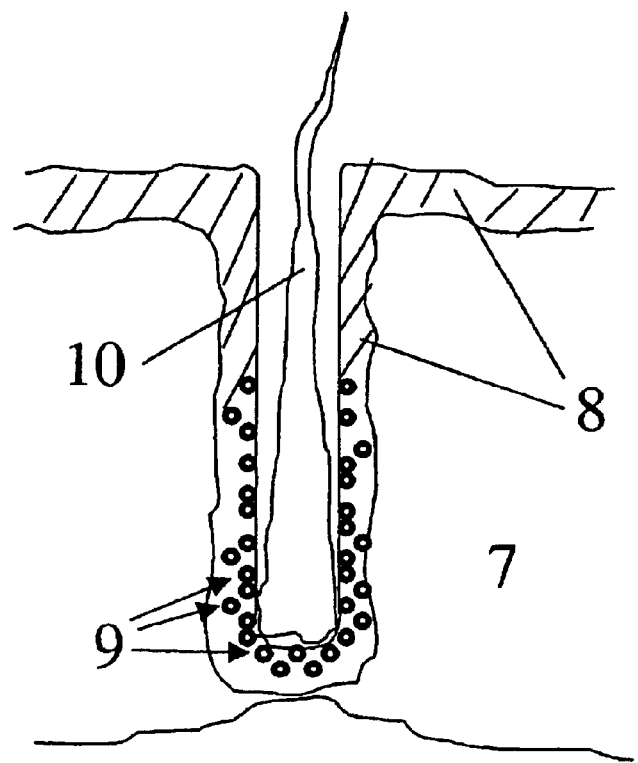
FIG. 4b depicts a sectional view of the implant site after the filament core (1) has been removed by pulling out the semi-rigid backing (4) to which it is attached out of the dermis (7) and epidermis (8). Note the resulting separation of the porous, cultured cell laden sheath (2) from the core. As shown in this figure, the implanted sheath has been present for a long enough time that new matrix cells (9) are beginning to elongate a new hair shaft (10).
Figure 5A:
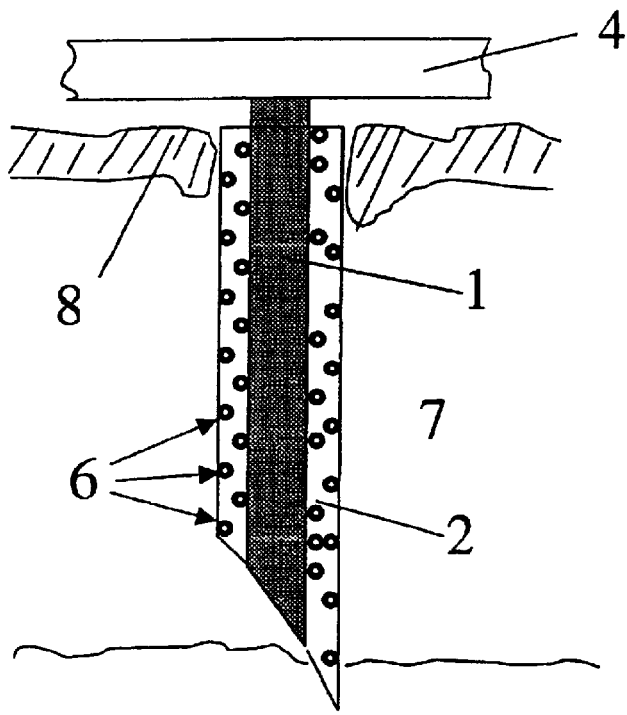
FIG. 5a depicts a sectional view of a single filament with cultured cells (6) contained within the porous sheath (2) surrounding the solid core (1) of the filament, which has been implanted in the skin through the full thickness of the dermis (7). In this case the filament is shown in the state in which it would be if it had been present in the skin only long enough for the porous coating to soften and detach from the solid core, but not long enough for the epidermis (8) to grown down the outside of the filament.
Figure 5B:
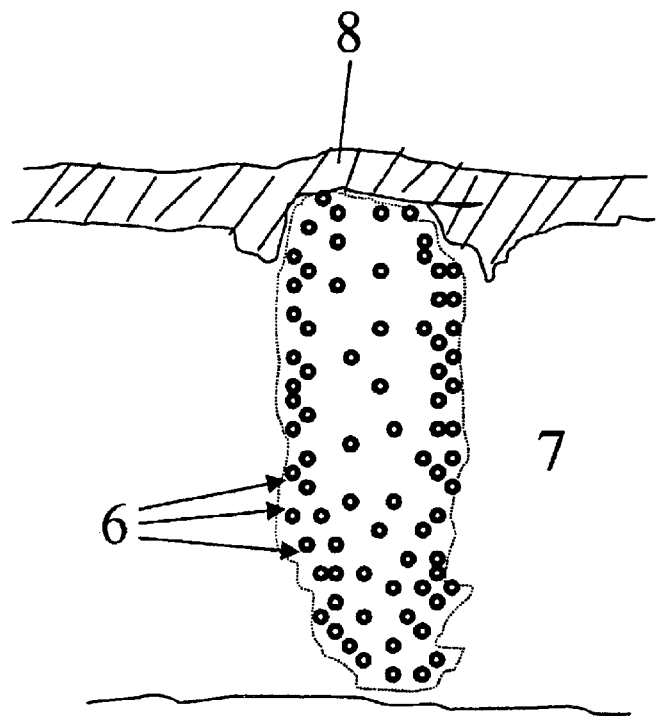
FIG. 5b depicts the implant site after the filament core has been removed by pulling out the semi-rigid backing to which it was attached as shown in FIG. 5a. In this case, pulling out the semi-rigid backing and core has resulted in separation of the cell laden porous sheath (2) from the solid core. Sufficient time has elapsed that the epidermis (8) has grown over the implant site, the porous bioabsorbable coating has resorbed, and the implanted cultured cells (6) have survived and are functioning properly.

Upon obtaining a plurality of fibers, each comprising a desired wire coated with a bioabsorbable porous sheath, the fibers are imbedded in a semi-rigid backing as follows. The first end of each fiber is placed in a mold. The mold is comprised of a block of any suitable material, such as Teflon™, with defining holes in a surface of the block that are just sufficiently large in diameter to accommodate the coated wires, and of a depth that corresponds to at least the desired depth that the first end of each fiber is to penetrate the skin when the hair follicle implant device is used to implant hair follicle cells into the skin of a living host. The spacing between the holes preferably corresponds to the spacing between hair follicles in the normal scalp. When the first end of each fiber is placed in the mold, the second end of each fiber protrudes from the surface of the mold. Once the plurality of fibers has been placed into the mold, a layer of silicone resin or other suitable liquid pre-polymer is then coated over the protruding second end of each filament and cured. The resulting implant device is preferably removed from the mold by placing a layer of adhesive tape with a backing that is puncture resistant over the cured resin, and then removing the tape therefrom. Removal of the tape pulls out the wires from the mold to yield the finished implant device (see FIG. 2). The implant device is preferably packaged in an appropriate container for protection of the delicate wires until use, and sterilized by ethylene oxide or other suitable means prior to use.

In order to use the above hair follicle cell implant device to regenerate hair follicles, a suspension of follicle progenitor cells is obtained. These cells can be harvested from some of the patient's normal follicles. Alternatively, progenitor cells can be obtained from the follicles of living donors or recently deceased organ donors. The finding that follicle progenitor cells were not rejected by an unrelated human recipient has been published by A. J. Reynolds, C. Lawrence, P. R. Caerhlmi-Friedman, A. M. Christiano, and C. A. B. Jahoda, *Nature* 402: 33–34, Nov. 4, 1999, the teachings of which are incorporated herein.

Cells multiplied in a growth medium are loaded into the array of coated wires by seeding the porous sheath of the first end of each filament with the cells, preferably by wicking the growth medium containing the cells into the porous coatings. The cells optionally can be further multiplied by continuing the tissue culture process after seeding the porous sheath of each filament with the cells, to ensure that cell attachment and spreading within the porous matrix has occurred. The first end of each filament is then implanted into the dermis by pressing the seeded implantation device onto the skin, preferably after softening and anesthetizing the skin with the use of an analgesic lotion under an occlusive dressing such as Tegaderm™ (3M Company). After several days the bioabsorbable coating separates from the wire. The wires and semi-rigid backing can then be removed by pulling off the tape to which they are attached, thereby leaving the porous bioabsorbable matrix and attached follicle cells in the dermis. New hair follicles are generated in the implant sites as the transplanted cells multiply and sort themselves into the appropriate functional layers under the influence of the follicular stem cells carried through from the original donor follicles. Each new hair follicle will then grow a hair shaft in the space that was formerly occupied by the wire. The hair will have the same color and consistency as the donor hair that was used to create the cell culture. The hair follicle cell donor is preferably the living host, and the hair regenerated thereby has the same color and consistency as that of the host.

Gene Therapy and Encapsulated Cell Delivery.

In a related embodiment of the present invention, the cells that are obtained from hair follicles of a living host can be genetically modified to express gene products that benefit the living host when implanted therein. Because the hair follicle cells are rapidly multiplying and renewing themselves as hair grows, the genetically modified cells implanted as described above will serve as a permanent and continuous source of needed substances. An example of such a substance is factor IX which would provide a cure for hemophilia B. In this case, new hair growth may not be needed on the scalp and instead could be established on other parts of the body such as on the back or the legs. The follicles harvested to produce the genetically engineered cultured cells can be taken from the same skin in which the new hair will be created. Thus the cosmetic effect of the presence of this superfluous new hair growth will be insignificant.

In another embodiment, cells that do not produce hair such as dermal fibroblasts can be similarly implanted in the skin. These cells would be suitable for achieving a temporary therapeutic effect. For example, bed sores, also known as decubitus ulcers, are a significant cause of patient discomfort, infection risk, and health care cost in nursing homes. Another major medical problem is non-healing skin ulcers primarily found on the lower extremities of patients with poor circulation due to disease such as diabetes. It is well known that growth factors such as platelet derived growth factors are capable of facilitating rapid wound healing but cannot heretofore be conveniently administered to ulcers that are exuding fluid. In this embodiment of the present invention, fibroblasts or other suitable cells are genetically modified to express the desired growth factors and are implanted into the ulcer, thereby stimulating tissue regeneration and healing the ulcers.

Other disorders and diseases of the skin that can be treated with similar embodiments include lamellar ichthyosis, a disfiguring skin disease characterized by abnormal epidermal differentiation and defective cutaneous barrier function. This skin disorder is caused by the deficiency of an enzyme known as keratinocyte transglutaminase1 (Tgase1), the replacement of which is a potential future approach to therapeutic gene delivery in human skin. Thus dermal keratinocytes can be genetically engineered to express the needed enzyme and implanted into the skin by the methods of the present invention.

In another embodiment, cells that have a very slow rate of division but provide an essential function can be transplanted from one part of the body of a donor into the skin of a living host. Once transplanted, the cells will benefit from the high vascularity of the surrounding tissue. An important example is the transplantation of pancreatic islet cells as a treatment for diabetes. When the donor and host are not the same individual, as is the case when pancreatic islet cells are transplanted into a living host suffering from diabetes, the cells must typically be immunoprotected by encapsulation prior to transplantation. Encapsulation prevents the patient's antibodies from destroying the foreign cells, while allowing lower molecular weight substances including insulin and glucose to diffuse in and out of the capsules containing the donor cells.

A serious deficiency of methods of the prior art of introducing such encapsulated cells into the patient is the difficulty of both delivering a large number of cells and providing a high surface area implant to ensure good exchange with the blood supply. Thus, encapsulated cells of the prior art have been implanted in a manner that resulted in an inadequate survival rate and an insufficient output of insulin to cure diabetes. The present invention solves these problems by providing a more effective means for the delivery of encapsulated cells. Thus a multitude of small implants each comprising only a few layers of encapsulated cells delivered by the methods of the present invention ensures that the donor cells receive optimal nutrition from the vasculature of the dermis and provide an efficacious, glucose responsive release of insulin into the blood stream.

Bone Regeneration.

Figure 6:
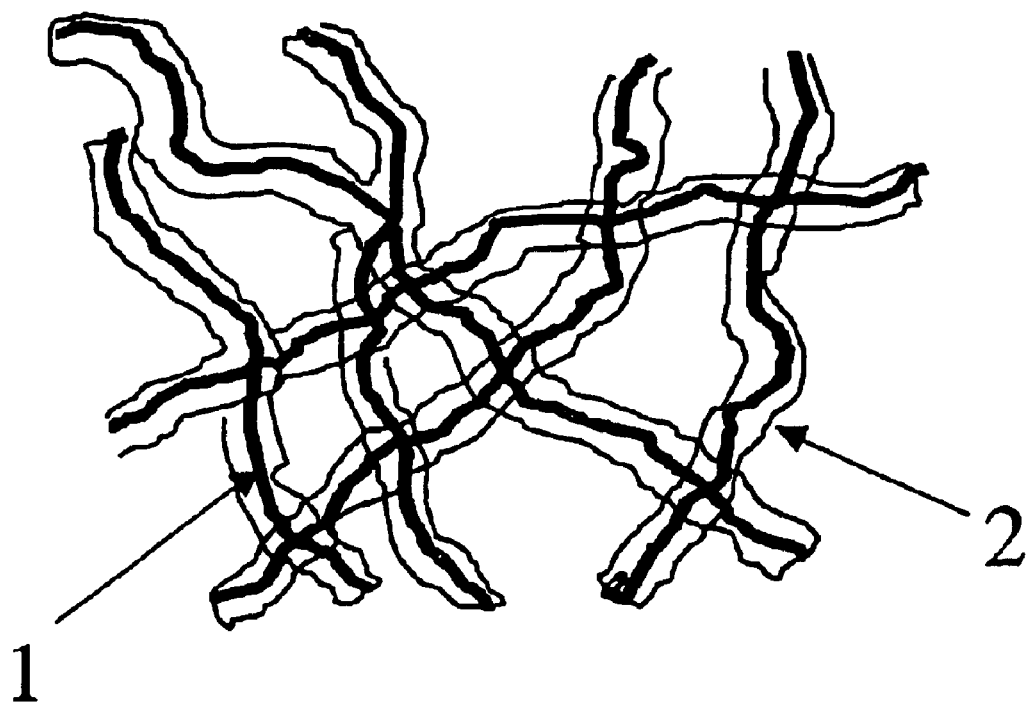
FIG. 6 is a schematic representation of filaments comprised of a solid core (1) and a porous coating (2) that are bonded together. The process that is utilized to create the bonds between the filaments, for example by heating and cooling, preferably is the same process that is used to create porosity in the coating.

In another embodiment of the present invention, fibers of the present invention are fused together in a three dimensional structure which provides a highly porous matrix for bone regeneration (see FIG. 6). In addition to the porosity created by the spaces between the fibers which is beneficial for bone ingrowth, the high surface area of the porous coating on the fibers facilitates osteoblast attachment. This allows the option of seeding the material with osteoblasts to provide a tissue engineered implant. In this case the porous coating is preferably selected from polycarbonates such as poly(trimethylene carbonate) and tyrosine-desaminotyrosine derived polycarbonates due to their excellent compatibility with new bone and the absence of acidic degradation products that may contribute to bone resorption or inflammation late in the bioabsorption process. The core fiber is preferably a biocompatible, osteoconductive ceramic or glass such as those known as "bioglass". The fiber may also be selected from a number of slowly dissolvable or bioabsorbable glasses such as calcium metaphosphate glasses.

The process for making the bone regeneration matrix involves providing an osteoconductive ceramic or glass fiber and coating said fiber with a mixture of polymer and blowing agent. The coated fibers are then cut into short lengths and formed into a nonwoven web by any of several known methods. The web is then formed into the desired shape and heated at a temperature that-both melts and fuses the coating on the fibers and decomposes the blowing agent to yield a reticulated foam structure. The solid inorganic fibers are unaffected by this process other than becoming glued together to form a rigid structure. The device can then be sterilized, seeded with cells, and stored in a frozen state until needed for implantation to regenerate bone. The surgeon can then sculpt the material just prior to implantation so that it fits into the bone defect. If the material is to be used to regenerate bone within a spinal fusion device, such as an interbody fusion "cage", the matrix can be pre-formed to fit exactly the dimensions of the cage.

Trans-Dermal Drug Delivery.

Another embodiment of the present invention is a trans-dermal drug delivery device, and a method of using the device. Many drugs could benefit from trans-dermal delivery but lack the properties that are required for penetration of the skin. The present invention overcomes this problem by providing a physical path through the stratum corneum and into the dermis.

The trans-dermal drug delivery device of the present invention comprises a semi-solid backing with a plurality of filaments fixed therein, wherein each filament comprises a wire core coated by a porous polymer sheath in which the drug is soluble and permeable. Each filament has a first end and a second end. The second end of each filament is fixed in the semi-solid backing, such that the first end of each filament protrudes from one surface of the semi-solid backing. The semi-solid backing further comprises a drug reservoir which is in contact with the second end of each filament.

When the trans-dermal drug delivery device of the present invention is applied to the skin of a living host, the first end of each filament penetrates the outermost barrier layer of the skin and allow the drug to diffuse slowly through the porous sheath of each filament into the blood stream of the living host.

The trans-dermal drug delivery device of the present invention is preferably made according to a method similar to the method described above for producing the hair follicle cell implantation device of the present invention, disclosed above. In the present case, the second ends of each of the plurality of filaments are set in holes in a release liner film corresponding to mold cavity holes that are not as deep as those used to make the hair follicle cell implantation device. The polymer resin that is used to cover the protruding wire ends is a pressure sensitive adhesive with drug blended in, and the puncture resistant backing has adequate moisture vapor transmission for long term coverage of the skin. The device is then sterilized and packaged. To use the device the patient simply separates the protective release liner from the backing, thereby exposing the coated wires and drug/adhesive surface, and applies this to the skin in the same manner as with other transdermal drug delivery patches.

Alternatively, when the drug to be delivered with the trans-dermal drug delivery device of the present invention has a very low solubility in the polymer used to make the porous sheath of the filaments, the drug can be mixed with the coating polymer as a suspension prior to formation of the porous sheath. In this case a slow release of the drug is provided directly to the dermis from the drug loaded coating and from there into the blood stream. Suitable coating polymers for use in the drug delivery application include bioabsorbable hydrogels that have porosity on a molecular scale.

EXAMPLE 1

Porous Coated Wires for Implantation of Follicle Progenitor Cells

An array of 21 wires, 0.0035 inches in diameter (nickel-chromium alloy, California Fine Wire Co., Grover Beach, Calif. 93433), was made by imbedding the wires in epoxy resin contained in the cut-off end of a tuberculin syringe. The wires were first placed in a 2 mm thick disc with 0.0063 inch diameter holes arranged in a pattern of one surrounded by 7 surrounded by 13. The wires were pushed into the disc until flush with the surface. The opposite surface had various lengths of wire protruding. This surface was placed in contact with the liquid epoxy resin mixture such that the protruding wires became imbedded. The surface of the disc in contact with the epoxy was first coated with a thin layer of petrolatum to prevent adhesion. Upon curing of the epoxy resin, the disc was pulled off to expose 21 wires extending exactly 2 mm from the surface of the 4.5 mm diameter plug of epoxy resin.

A mixture of poly(dl-lactide-co-50%-glycolide) (Resomer™ RG504, Boehringer Ingelheim, D-55216 Ingelheim am Rhein, Germany) and 5% by weight of azodicarbonamide (Aldrich Chemical Co., Milwaukee, Wis. 53201) was melt blended by stirring in a test tube immersed in an oil bath maintained at a temperature of 180° C. A small amount of this mixture was placed in the bottom of a 50 ml beaker and re-heated to give a viscous liquid. The above epoxy resin plug was inverted and the wires dipped into the molten polymer mixture to a depth of about 0.3 mm and quickly removed. This produced a thin coating of polymer mixture on the tips of the wires and fine filaments pulled away from the melt and attached to the tips.

Figure 7:
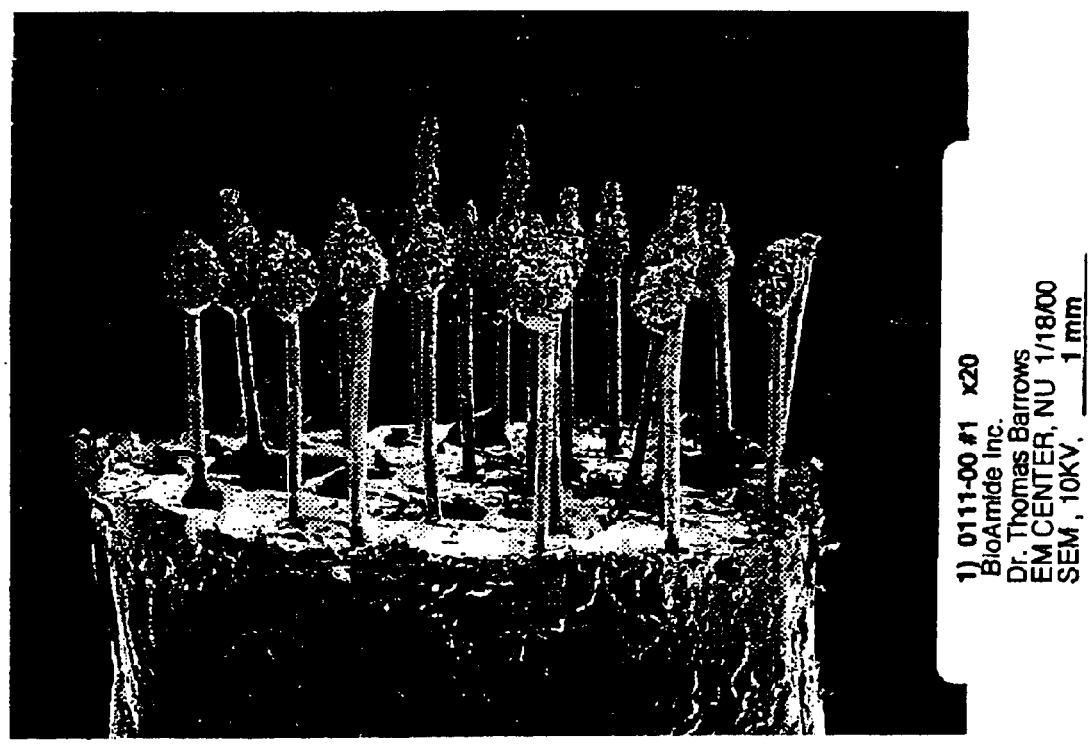
FIG. 7 is a scanning electron micrograph (SEM) of the device described in Example 1, at a scale of 1 mm.
Figure 8:
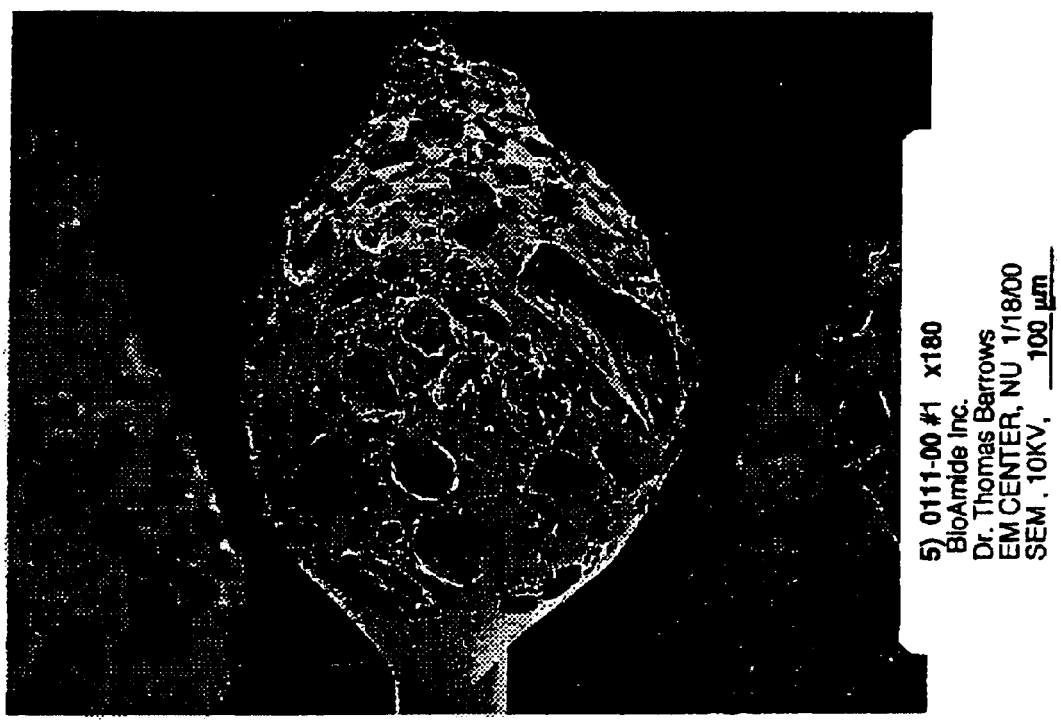
FIG. 8 is an SEM of the device described in Example 1, viewing the wires on end showing the exposed tips of the wires and the surrounding coatings of porous, bioabsorbable polymer, at a scale of 100 $\mu$m.
Figure 9:
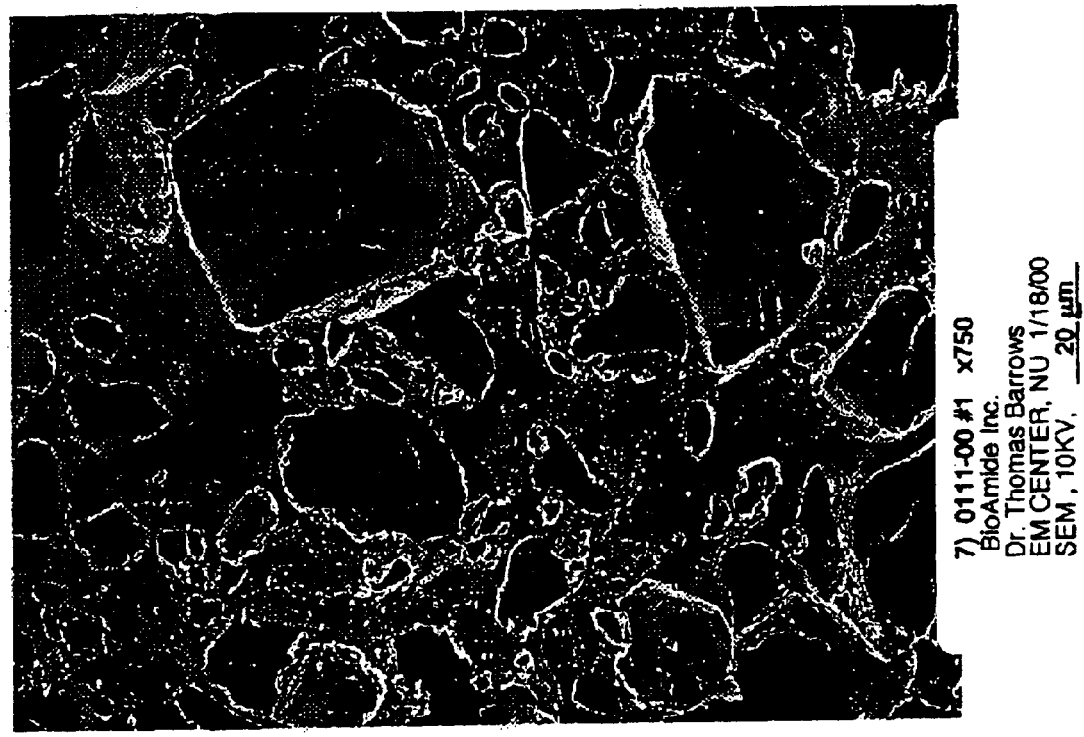
FIG. 9 is an SEM of the end of a single wire of the device described in Example 1, showing the morphology of the porous coating, at a scale of 20 $\mu$m.

Crystals of sodium chloride (Morton Popcorn Salt) were placed in an electric coffee bean grinder and milled into a fine powder. A ½ inch diameter hex bolt was placed on end and a nut threaded onto the bolt just far enough to engage the threads. The cavity formed by the nut and bolt was filled with powdered salt. A thermometer was lowered into the salt and clamped in a vertical position with clamps on a ring stand. The surface of the salt was smoothed out with a spatula. The bolt was heated with a propane torch until the temperature of the salt reached 240° C. The polymer-coated wires were then dipped into the hot salt, pushed about half way in and then quickly pulled out. The adherent salt was removed by dipping the wires in water until the salt dissolved. The water was removed from the device by gently blotting with tissue paper. The device was placed back in a tuberculin syringe barrel for protection and stored in a desiccator. Scanning electron micrographs of device are shown in FIGS. 7–9.

EXAMPLE 2

Use of the Device of EXAMPLE 1 to Produce New Hair Follicles

The device of Example 1 is soaked in ethanol for 5 minutes and then rinsed with sterile water. The excess water is removed from the porous structure by blotting with a sterile, lint-fee surgical sponge. This process serves both to sterilize the polymer and to improve the ability of cells to be wicked rapidly and completely into the porous polymer.

Human dermal papilla cells that have been multiplied in culture are collected and resuspended in an isotonic buffer solution at approximately ten million cells per cubic centimeter. The pre-wet implant is then dipped into the suspension of cells and immediately injected into human skin where the growth of hair is desired.

Prior to implantation, the skin is wiped with gauze soaked in 70% isopropanol and then wiped with gauze soaked in Betadine™. Lidocaine cream is then applied to the skin and covered with a Tegaderm™ dressing for a minimum of one hour. This pre-implantation procedure serves to kill bacteria and to soften and anesthetize the skin. After implanting the device, the exposed epoxy resin plug is covered with a dressing to prevent it from being disturbed or dislodged.

Approximately 48 hours after implantation, the dressing is removed. The wires are then removed from the skin by pulling on the epoxy resin plug. The cell-laden porous bioabsorbable polymer lips remain under the skin, having separated from the wires as a result of tissue attachment to the porous polymer and moisture induced loosening of the polymer attachment to the metal.

During the next period of several weeks the implanted cells multiply and organize into a new hair follicle as the bioabsorbable polymer degrades and is bioabsorbed. The growth of new hair indicates that the restoration process is complete.

EXAMPLE 3

Porous Scaffold for Tissue-Engineered Bone

Poly(70%-L-lactide-co-30%-d,l-lactide) obtained from Purac Biochem, b.v. (Gorinchem, Holland) is melt blended at about 170° C. with 5% by weight azodicarbonamide (Aldrich Chemical Co.) and pelletized. A proprietary bioabsorbable glass fiber produced by MO-SCI Corp. (Twitty Industrial Park, Rolla, Mo. 65401) is obtained as a monofilament single strand that is 100 microns in diameter.

A cladding extrusion die is made such that the 100 micron diameter fiber can pass through the die while polymer is extruded to cover and clad the moving fiber. The polymer/azodicarbonamide blend is extruded as a cladding on the glass to give a cross-sectional area ratio of 2:1 core to sheath.

The fiber is cut into 3 to 5 millimeter lengths and added to a beaker of water with stirring. The resultant slurry is then poured onto a Buchner funnel equipped with a coarse glass frit and the water allowed to drain. This produces a "wet-laid" non-woven web of fibers. The web is dried under vacuum and carefully transferred into a wire basket. The basket is lowered into a beaker of peanut oil heated to 240° C. for about one second and then immersed in a beaker of hexane. The hot oil causes the polymer to melt and the azodicarbonamide to decompose into gas, thereby converting the polymer into an open-cell foam. The cool hexane causes the polymer to solidify, thereby preserving the porous structure and adhering the glass fibers together at every point that they touch. The hexane also dissolves and removes the oil from the structure without affecting the polymer.

Chondrocytes are seeded onto the structure from an aqueous suspension causing the cells to wick into the porous polymer coating on the glass fibers. The structure can then be implanted in a bone defect immediately or allowed to mature in culture prior to implantation. In either case the cells will be retained in the microporous structure of the coating while the macroporous structure of the adhered fibers will allow ample room for tissue ingrowth and osteoinduction of new bone due to the seeded cells.

While the present invention has now been described with some detail and specificity, those skilled in the art will appreciate the various modifications, including variations, additions, and omissions, that may be made in what has been described. Accordingly, it is intended that the scope of the present invention be limited solely by the broadest interpretation that lawfully can be accorded the appended claims.

What is claimed is:

1. A filamentary structure for the introduction of an agent into a living host, comprising a filament comprising a solid core and a porous sheath, and an agent selected from the group consisting of hair follicle cells, genetically engineered cells, encapsulated cells, and cell signaling molecules, wherein the solid core comprises a metal or an alloy and wherein the porous sheath comprises a bioabsorbable sheath polymer which coats at least a portion of the solid core.

2. The filamentary structure of claim 1, wherein when the solid core is made of a biocompatible material selected from the group consisting of metals or alloys containing the elements of iron, nickel, aluminum, chromium, cobalt, titanium, vanadium, molybdenum, gold, and platinum.

3. The filamentary structure of claim 1, wherein the bioabsorbable sheath polymer is selected from the group consisting of poly(lactic acid), poly(glycolic acid), poly (trimethylene carbonate), poly(amino acid)s, tyrosine-derived poly(carbonate)s, poly(carbonate)s, poly(caprolactone), poly(para-dioxanone), poly(ester)s, poly(ester-amide)s, poly(anhydride)s, poly(ortho ester)s, proteins, carbohydrates, poly(ethylene glycol)s, poly (propylene glycol)s, poly(acrylate ester)s, poly(methacrylate ester)s, poly(vinyl alcohol), and copolymers, blends and mixtures of said polymers.

4. The filamentary structure of claim 1, wherein the agent is hair follicle cells.

5. The filamentary structure of claim 1, wherein the agent is genetically engineered cells.

6. The filamentary structure of claim 1, wherein the agent is encapsulated cells.

7. The filamentary structure of claim 1, wherein the agent is cell signaling molecules.

8. The filamentary structure of claim 1, wherein the agent is coated on the outer surface of the porous sheath.

9. The filamentary structure of claim 1, wherein the agent is mixed, dissolved, or imbedded within the porous sheath.

10. The filamentary structure of claim 1, wherein porous sheath defines open pores which are substantially interconnected and large enough to admit the agent.

11. The filamentary structure of claim 10, wherein the open pores are large enough to admit molecules ranging in molecular weight from about 500 to about 100,000 Daltons.

12. A method of making a filamentary structure for introducing an agent into a living host, comprising the steps of:
   a) providing a filamentary solid core,
   b) providing a bioabsorbable polymer,
   c) providing a pore-forming agent,
   d) mixing said bioabsorbable polymer with the pore-forming agent,
   e) coating said mixture onto the solid core,
   f) substantially removing or decomposing the pore-forming agent;
   g) loading the filamentary structure with an agent selected from the group consisting of hair follicle cells, genetically engineered cells, encapsulated cells, and cell signaling molecules; and
   wherein the solid core comprises a metal or an alloy.

13. The method of claim 12, wherein the bioabsorbable polymer is poly(L/DL-lactide).

14. The method of claim 12, wherein the pore-forming agent provided in step (c) is azodicarbonamide.

15. The method of claim 12, wherein the pore-forming agent provided in step (c) is urea dicarboxylic acid anhydride.

16. The method of claim 12, wherein coating step (e) is performed by melt extrusion.

17. The method of claim 12, wherein steps d) and e) are performed by additional steps comprising:
   dissolving said mixture of the bioabsorbable polymer and the pore-forming agent in a polymer solvent to form a solution,
   coating at leant one end of the solid core by placing it in the solution, and
   removing the solid core from the solution.

18. The method of claim 17, wherein the polymer solvent is also the pore-forming agent.

19. The filamentary structure of claim 3 wherein the protein is selected from the group consisting of collagen, gelatin, and serum albumin.

20. The filamentary structure of claim 4, wherein the hair follicle cells are cultured.

21. The filamentary structure of claim 5, wherein the genetically engineered cells are cultured.

22. The filamentary structure of claim 6, wherein the encapsulated cells are cultured.

* * * * *